United States Patent [19]

Augustin

[11] Patent Number: 4,712,418

[45] Date of Patent: Dec. 15, 1987

[54] APPARATUS FOR THE MEASUREMENT OF SURFACE FRICTION

[76] Inventor: Harald Augustin, Arsenal Objekt 7/4/16, A-1030 Wien, Austria

[21] Appl. No.: 833,207

[22] Filed: Feb. 26, 1986

[30] Foreign Application Priority Data

Feb. 26, 1985 [AT] Austria ................................ 569/85

[51] Int. Cl.⁴ .................... G01N 19/02; G01L 5/00
[52] U.S. Cl. ........................................ 73/9; 73/10; 73/146
[58] Field of Search ................... 73/9, 10, 146, 8, 7

[56] References Cited

U.S. PATENT DOCUMENTS

| | | | |
|---|---|---|---|
| 2,441,993 | 5/1948 | Dasher | 73/9 X |
| 3,823,599 | 7/1974 | Litz et al. | 73/10 |
| 4,051,713 | 10/1977 | Bao et al. | 73/9 |
| 4,594,878 | 6/1986 | Abe et al. | 73/9 |

FOREIGN PATENT DOCUMENTS 2326954 12/1974 Fed. Rep. of Germany ............ 73/8

Primary Examiner—Tom Noland
Attorney, Agent, or Firm—Fleit, Jacobson, Cohn & Price

[57] ABSTRACT

Apparatus for the measurement of surface friction of surfaces, in particular of surfaces designed for traffic, such as road surfaces, floor coverings, and similar surfaces. The apparatus includes a supporting assembly that can be positioned on the surface to be measured, and the supporting assembly supports a shaft of a rotor that is rotatable about an axis perpendicular to the surface and carries at least one contact member. A measuring device is provided for the measurement of the torsional resistance to rotation of the rotor as a result of contact between the contact member and the surface.

4 Claims, 1 Drawing Figure

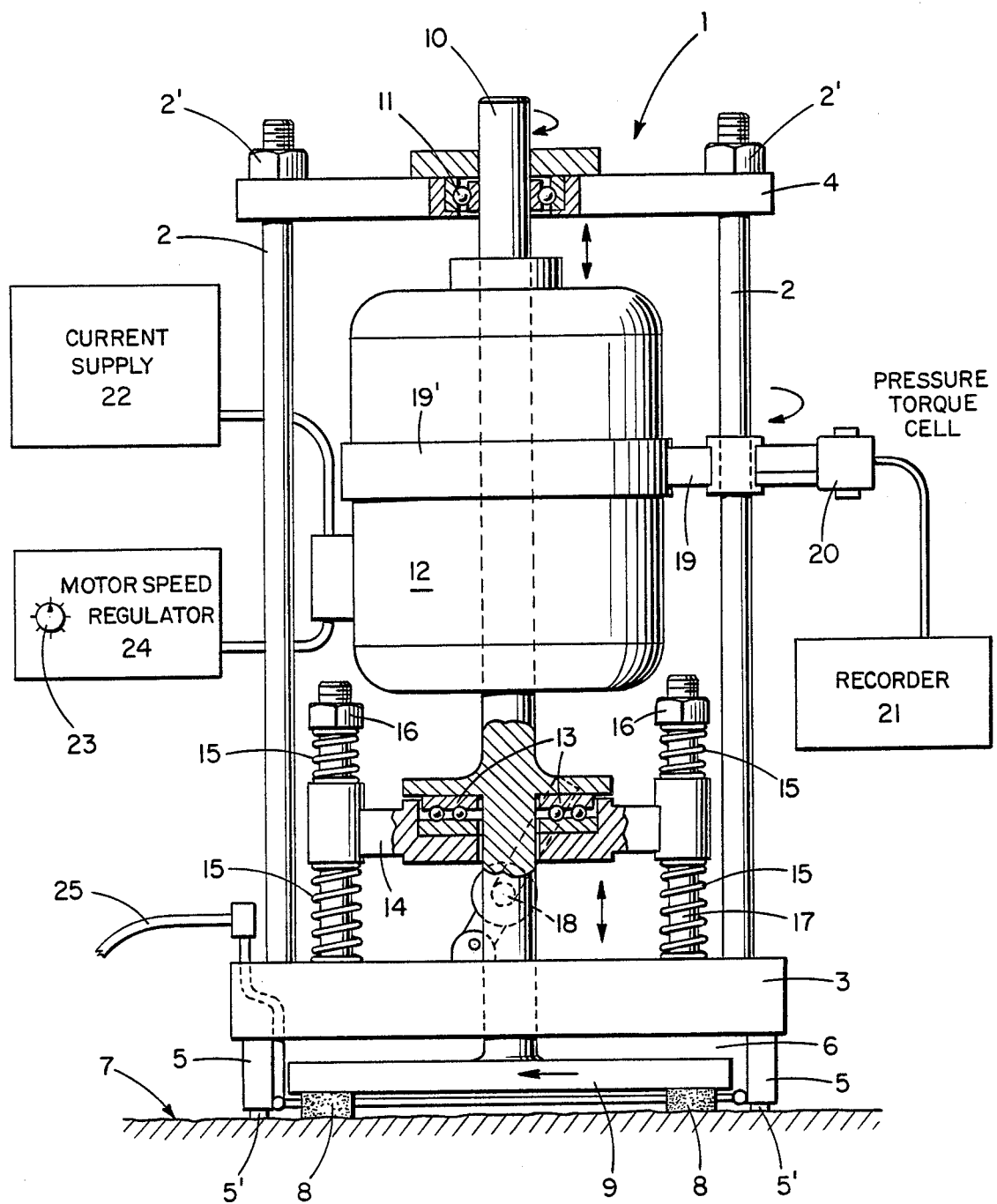

APPARATUS FOR THE MEASUREMENT OF SURFACE FRICTION

BACKGROUND OF THE INVENTION

The invention relates to an apparatus for the measurement of surface friction, in particular of surfaces designed for traffic, such as road surfaces and similar surfaces, but also of floor coverings in buildings, garages, and the like.

It is desirable to provide a friction measuring apparatus that can be produced at comparatively low cost, that is distinguished by a strong and simple design and that is simple to operate, so that it can be moved easily from one site of operation to another, because of low weight and small overall size.

SUMMARY OF THE INVENTION

In accordance with one aspect of the invention, a friction measuring apparatus includes a supporting assembly that may be positioned on the surface the friction of which is to be tested. The assembly supports the shaft of a rotor that is adapted to rotate around an axis that is perpendicular to the surface to be measured and the rotor is equipped with at least one contact member to contact the surface. A measuring device is carried by the supporting assembly for the measurement of the torsional resistance that is transferred to the rotor as a result of contact between the contact member of the rotor and the surface to be measured.

The frictional resistance of the two, three, or more contact members which are distributed centro-symmetrically over the periphery of the rotor is converted into a torque that can be measured by the measuring device, and is transmitted by the rotor shaft, whereby the valuable advantage results that the carrying stresses on surfaces of the wheels of vehicles or of similar objects can be simulated simply by adjusting the pressure on the rotor.

An additional result is the equally valuable advantage that any atmospheric or physical conditions prevailing in practice, in particular weather conditions, can be simulated in a very simple way in the space enclosed by the supporting assembly and adjacent to the surface, so that measurements of surface friction can be achieved for totally different conditions.

To that end, the rotor is mounted, in accordance with a preferred form of embodiment of the object of the invention, on the lower end of a rotor shaft which is arranged within the supporting assembly in such a way that its height can be varied, and it may be set against the surface with adjustable pressure.

In addition, a supply pipe for a liquid, such as water, an oil-water emulsion, ground maintenance materials, or the like, may be linked up with a space that is enclosed by the supporting assembly of the rotor shaft within the area of the rotor and which may, if need be, sealed off.

BRIEF DESCRIPTION OF THE DRAWING

The single drawing FIGURE shows a side elevational view of an example of the embodiment of an apparatus in accordance with the invention.

DESCRIPTION OF THE PREFERRED EMBODIMENT

Referring now to the drawing, the apparatus includes a supporting assembly 1 that consists of two or more uprights 2, the lower ends of which have been screwed into a base 3, and the upper ends of which are fastened onto a crossbeam 4 (which can also be in the form of a cover plate) by means of threaded holding nuts 2' and secured thereby. The base 3 rests on a base ring 5, the underside of which supports a gasket 5' and encloses a space 6 that is sealed thereby, and inside which a rotor 9 is positioned. Rotor 9 may be placed on a surface 7, for example on the top of a traffic surface, and is equipped with contact members 8. The contact members 8 may be made of rubber or plastic materials, and they present in front, in the sense of the direction of rotation of the rotor 9, a slanting or rounded tread or contact surface, to thereby establish contact with the surface 7 in a manner similar to an automobile tire.

The rotor 9 is mounted on the lower end of a rotor shaft 10 that extends along the full height of the supporting assembly 1, and is supported at its upper end in bearing 11 of the crossbeam 4 in such a way that it can be moved axially.

Rotor shaft 10 coaxially supports the rotor of an electric drive motor 12. By means of a fixed bearing 13, that is, a bearing that cannot be moved axially along the shaft 10, the rotor shaft 10 is held in a mounting support 14, the position of which is controlled by helical springs 15 that have their axes arranged in parallel. The pressure exerted by the helical springs 15 on the mounting support 14, and thereby on the rotor 9 by way of the rotor shaft 10 and against the surface 7, may be adjusted at will by means of threaded adjusting nuts 16 which serve as the upper support for the helical springs 15 and are screwed on the spring bolts 17 mounted in the base 3. Instead of springs, a suitable hydraulic device can be provided for exerting axial pressure on rotor shaft 10.

An adjusting device that can be actuated by means of a lever 18 pivotally mounted to base 3 makes it possible to raise the rotor 9 from an operating position, as shown in the drawing, in which contact members 8 lie on the surface 7 with adjustable pressure, into a resting position in which contact members 8 are spaced from surface 7.

The motor 12, which exerts the torque required for the rotation of the rotor 9 carried by the rotor shaft 10, is restrained from itself rotating by means of an arm 19 that extends radially outwardly from the motor stator or casing to one of the uprights 2, while a torque-meter, for example a pressure cell 20, can be mounted to measure the torque between arm 19 and upright 2. Arm 19 is fastened onto the casing of motor 12 by means of a clamping collar 19'. Pressure cell 20 measures the torque exerted by the rotor 9 on the surface 7, and thereby the frictional resistance of surface 7. However, within the framework of the invention, it is possible also to use, instead of such a pressure cell or torque-meter 20, any other device for the measurement of torque, for example a torque-measuring device (not shown) that is directly connected with the rotor shaft 10.

If desired, the measurement results provided by the torque meter or pressure cell 20 can be recorded by a suitable recording device, such as by recording device 21.

The motor 12 is supplied with current by a conventional stationary or portable source of current 22, and a speed-regulating device 24 is provided to regulate the speed of the motor and can include a thyristor 23.

In order to be able to test and measure the friction of the surface 7 under special conditions, a conduit or supply pipe 25 for supplying any chosen liquid, for example water, oil emulsion, cleaning fluids, and the like, can be connected with the space 6 that is enclosed by base ring 5 of the supporting assembly 1 of the rotor shaft, and that is sealed by the gasket 5'.

It is to be understood that the details of the invention can be varied in many ways, and the invention is not restricted to the details and characteristics shown and discussed in the example of its embodiment.

What is claimed is:

1. Apparatus for the measurement of the friction of surfaces designed for traffic, such as road surfaces, floor coverings, and similar surfaces, said apparatus comprising:
   a supporting assembly that can be positioned on the surface to be measured,
   drive means carried on said supporting assembly and including an output shaft,
   a rotor secured to said output shaft and having an axis of rotation that is perpendicular to the surface and having at least one contact member for contacting the surface,
   adjustable pressure means carried by said support assembly for adjusting the contact force between the contact members and the surface, and
   measuring means for measuring the torsional resistance to rotation of the drive means as a result of frictional contact between the contact member and the surface to be measured,
   wherein said drive means is positioned coaxially with said rotor and included a motor casing, restraining means extending from said motor casing in a plane substantially perpendicular to the rotor axis and against the supporting assembly to prevent angular motion of the motor casing, said measuring means operative for measuring the torsional resistance exerted by the motor casing on the supporting assembly and mounted to measure the torque between the restraining means and the supporting assembly.

2. Apparatus in accordance with claim 1, including bearing means that supports and axially restrains the rotor and is connected with said spring means.

3. Apparatus in accordance with claim 2, wherein said apparatus includes adjusting means for moving the rotor axially from an operating position in which the contact member rests on the surface, into a resting position in which the contact member is spaced from the surface.

4. Apparatus for the measurement of the friction of surfaces designed for traffic, such as road surfaces, floor coverings, and similar surfaces, said apparatus comprising:
   a supporting assembly that can be positioned on the surface to be measured,
   drive means carried on said supporting assembly and including an output shaft,
   a rotor secured to said output shaft and having an axis of rotation that is perpendicular to the surface and having at least one contact member for contacting the surface,
   adjustable pressure means carried by said support assembly for adjusting the contact force between the contact members and the surface, and
   measuring means for measuring the torsional resistance to rotation of the drive means as a result of frictional contact between the contact member and the surface to be measured,
   wherein said supporting assembly includes sealing means for defining an enclosed space beteen the rotor, the sealing means and the surface, and conduit means carried by said supporting means for supplying a liquid to the space that is enclosed by the sealing means in the area contacted by the contact member.

* * * * *